(12) United States Patent
Seedhom

(10) Patent No.: US 9,351,720 B2
(45) Date of Patent: May 31, 2016

(54) IMPLANTATION ASSEMBLY FOR A PROSTHETIC LIGAMENT

(71) Applicant: Xiros Limited, Leeds (GB)

(72) Inventor: Bahaa Botros Seedhom, Leeds (GB)

(73) Assignee: XIROS LIMITED, Leeds (GB)

( * ) Notice: Subject to any disclaimer, the term of this patent is extended or adjusted under 35 U.S.C. 154(b) by 74 days.

(21) Appl. No.: 14/032,498

(22) Filed: Sep. 20, 2013

(65) Prior Publication Data

US 2015/0088255 A1    Mar. 26, 2015

(51) Int. Cl.
*A61B 17/04*    (2006.01)
*A61F 2/08*    (2006.01)

(52) U.S. Cl.
CPC ..... *A61B 17/0401* (2013.01); *A61B 2017/0404* (2013.01); *A61F 2/0811* (2013.01)

(58) Field of Classification Search
CPC . A61F 2/08; A61F 2/0805; A61F 2002/0847; A61F 2002/0852; A61F 2/0811; A61F 2002/30688; A61B 17/04; A61B 17/0401; A61B 2017/0404
See application file for complete search history.

(56) References Cited

U.S. PATENT DOCUMENTS

| 5,306,301 A * | 4/1994 | Graf et al. ............... 606/232 |
| 5,769,894 A * | 6/1998 | Ferragamo ............... 606/148 |
| 2008/0287991 A1 | 11/2008 | Fromm |
| 2013/0085527 A1 | 4/2013 | Ferragamo et al. |

FOREIGN PATENT DOCUMENTS

| EP | 2238944 | 10/2010 |
| EP | 2581047 | 4/2013 |
| WO | 98/12991 | 4/1998 |
| WO | 98/12992 | 4/1998 |
| WO | 99/47079 | 9/1999 |

* cited by examiner

*Primary Examiner* — Christopher D Prone
*Assistant Examiner* — Rokhaya Diop
(74) *Attorney, Agent, or Firm* — Kirton McConkie; Evan R. Witt

(57) ABSTRACT

An implantation assembly (16) has a guide element (22) for a ligament (18); a pulling element (24) comprising a pulling loop (26); and a manipulating loop (28). The guide element has a pulling aperture (36) towards a leading end (32), a manipulating aperture (38) towards a trailing end (34), and a connecting arrangement (40) for the ligament. The pulling and manipulating loops pass through the respective apertures. When the guide element emerges from a bone tunnel mouth, the manipulating loop is used to manipulate the guide element to a position where it overlies the tunnel mouth. The manipulating loop is secured to the pulling element and arranged such that a tensile load can be applied to the pulling element without generating a tensile load in the manipulating loop which could otherwise cause the guide element to be manipulated towards the anchoring position during passage along the bone tunnels.

20 Claims, 7 Drawing Sheets

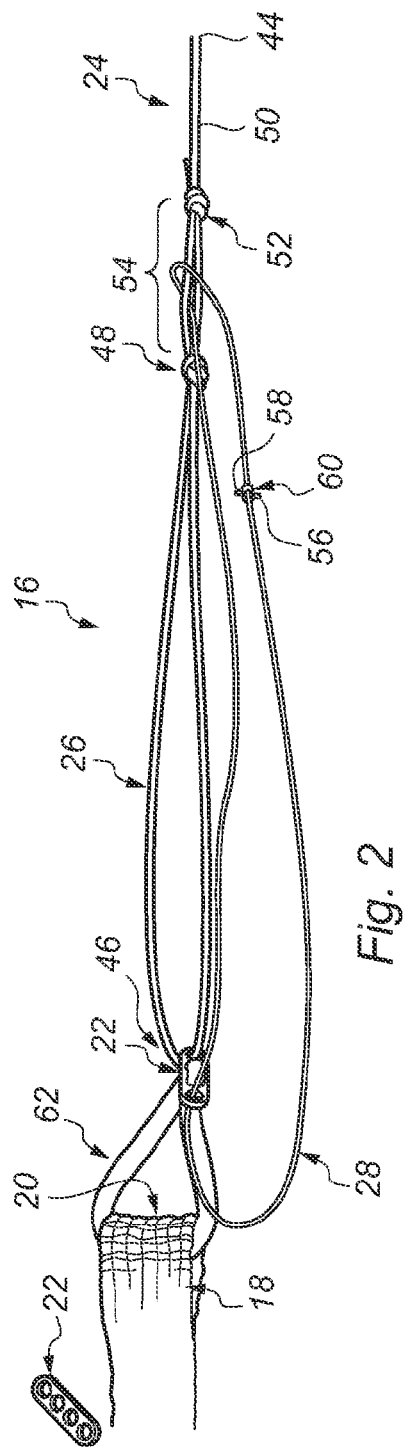
Fig. 2
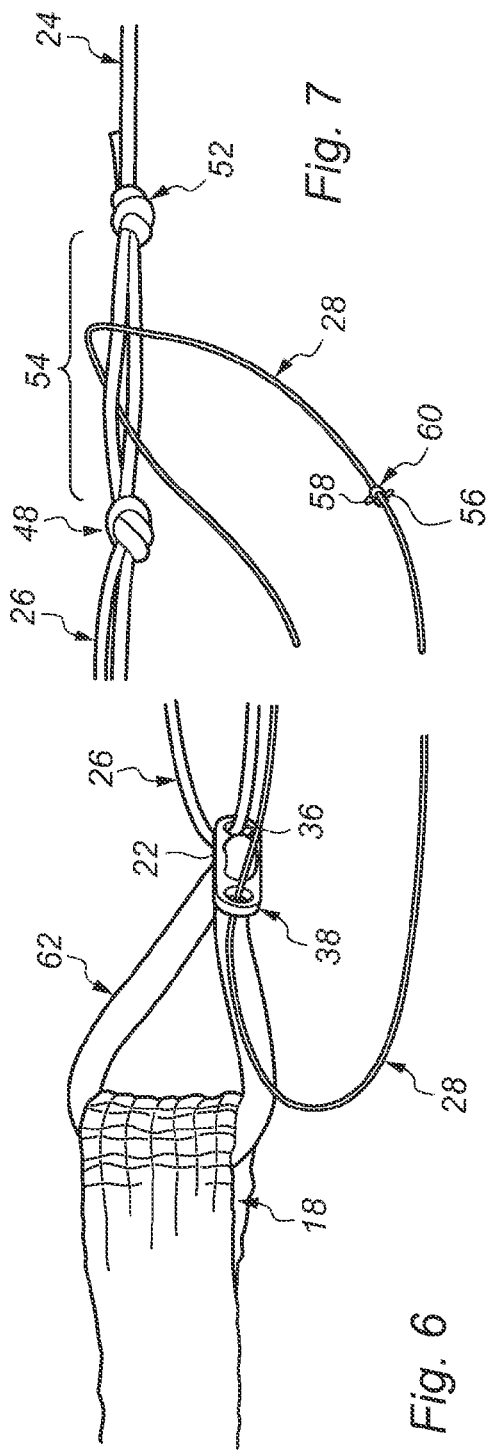
Fig. 7
Fig. 6

IMPLANTATION ASSEMBLY FOR A PROSTHETIC LIGAMENT

This invention is concerned generally with the implantation of a prosthetic ligament, and in particular with providing an improved implantation assembly for use in guiding a prosthetic ligament to a required position within a bone joint, and for anchoring one end of the ligament. The invention is also concerned with a corresponding method of implanting a prosthetic ligament at a required position in a bone joint.

In the implantation of a prosthetic ligament in a bone joint e.g. the knee joint between tibial and femoral components (bones), it is usual to drill tunnels through the bones, and to pull the prosthetic ligament through the tunnels until a required position is reached within the joint. The ligament is then anchored against linear movement in either direction. The anchoring may involve use of bone staples or other intrusive fixations, which attach tensile elements (connected to each end of the ligament) to suitable bone sites adjacent to the mouths of the bone tunnels.

Prosthetic ligaments can be made of synthetic material, provided that it is of a suitable implantable nature, and which may be woven. Alternatively, autogenous tissue harvested from the patient can be used, or allogenic tissue harvested from a suitable donor.

Prior endoscopic techniques developed for anterior cruciate ligament (ACL) reconstruction involved the use of a guide element which served both to guide the implantation of the ligament, and to secure one end of the ligament against axial movement in one direction. The guide element is of such a construction that it does not need to be anchored in position by physical intrusion into the bone.

The guide element used in these techniques provided easy guidance of the ligament, by forming the lead element of a trailing implantation system. The guide element passes through the drilled-out bone tunnels and, upon exiting an upper mouth of one of the tunnels (e.g. when it projects upwardly out of the femoral component), a simple manipulation of the device causes it to overlie the mouth of the tunnel. The guide element thus provided tensile restraint for the ligament attached to the guide element.

Guide elements of this type are known in the orthopaedic fraternity as 'Endobuttons™'. The guide element, or Endobutton™, is capable of being manipulated between a pulling position, in which it has a reduced lateral extent relative to the pulling direction, to an anchoring position, in which it has a maximum lateral extent relative to the pulling direction (for overlying the mouth of the bone tunnel).

The trailing assembly which followed pulling-through of the guide element typically comprised (a) further surgical cords (sutures) which were taken through a central pair of holes in the guide element, and then connected together to complete the formation of a loop by knotting together of the ends of the sutures, and (b) the prosthetic ligament (whether it was made of synthetic material or tissue, be this autogenous or allogenic) attached to, or suspended from, the looped sutures in any convenient manner.

The present inventor developed an improved attachment device including a guide element or Endobutton™ of this type in the 1990s, the device disclosed in International Patent Publication No. WO-98/12991A1. The main improvement on the prior design was the replacement of the knotted suture, from which the prosthetic ligament was suspended, with a captive knotless loop (or a non-captive variant of the same). Variants on the design of the guide element, and the means of connecting the knotless loops to it, were also disclosed.

The technique disclosed in WO-98/12991A1 involved the use of a pulling suture attached to the guide element through a first aperture, and a separate flipping suture attached to the guide element through a second aperture, which was spaced along the guide element. The pulling suture was used to pull the guide element through the bone tunnels as described above and, following emergence of the guide element from the tunnel mouth, the flipping suture was used to manipulate the guide element to overlie the mouth.

While the use of the use of knotless captive loops and their variants disclosed in WO-98/12991A1 provided distinct advantages over the prior techniques, in particular a superior strength over that of the prior knotted sutures, it is recognised that care must be taken during the use of the pulling and flipping sutures in order to avoid problems during implantation.

In particular, care must be taken to avoid causing the flipping suture to accidentally become tense, which can cause the guide element to jam slightly, particularly at the entrance of a bone tunnel. Such might occur, for example, if the surgeon accidentally pulled on the flipping suture during pulling of the guide element through the tunnels, or if the flipping suture became entangled with the pulling suture in such a way as to impart a flipping load on the guide element. Should the guide element jam at the tunnel entrance, dragging the guide element through the tunnel would then require greater application of force to the pulling suture, with an associated risk of breakage. If this should occur then it could bring about a delay in the surgery, whilst the pulling suture is replaced. If a replacement pulling suture was not available in the operating room, a surgeon might then need to use another device to complete the surgery. If this is not available in the surgical inventory, this could cause the surgery to be jeopardised or cancelled.

According to a first aspect of the invention, there is provided an implantation assembly for a prosthetic ligament, for guiding the ligament to a required position in a bone tunnel formed in a joint between two adjacent bones, and for anchoring one end of the ligament, the assembly comprising:

a guide element for the ligament, the guide element being manipulatable between a pulling position in which a longitudinal axis of the guide element extends generally parallel to a pulling direction and an anchoring position in which its longitudinal axis extends transversely of the pulling direction;

a pulling element comprising a pulling loop for pulling the guide element through the bone tunnels; and a manipulating loop for manipulating the guide element to overlie a mouth at an end of one of the bone tunnels;

in which:

in the pulling position, the guide element defines a leading end and a trailing end, a pulling aperture being provided towards the leading end, a manipulating aperture being provided towards the trailing end, and a connecting arrangement by which the ligament can be connected to the guide element being provided between the leading and trailing ends;

the pulling loop passes through the pulling aperture so that the pulling element can be used to pull the guide element and the trailing ligament through the bone tunnels with the guide element disposed in the pulling position;

the manipulating loop passes through the manipulating aperture so that, when the guide element emerges from the mouth at the end of the tunnel, the manipulating loop can be used to manipulate the guide element to the anchoring position where the guide element can overlie the tunnel mouth, to facilitate anchoring of the end of the ligament;

the manipulating loop is secured to the pulling element so that the manipulating loop can be pulled along the bone tunnels by the pulling element; and the manipulating loop is arranged such that a tensile load can be applied to the pulling element to pull the guide element, the trailing ligament and the manipulating loop through the bone tunnels without generating a tensile load in the manipulating loop which could otherwise cause the guide element to be manipulated towards the anchoring position during passage along the bone tunnels.

The invention addresses the potential difficulties with prior assemblies, because the pulling element and manipulating (or 'flipping') loop are configured in a way that removes the potential for the guide element to move towards the anchoring position, and so become 'snagged' in the bone tunnels, during transit towards the mouth of the tunnel. The pulling element and manipulating loop are effectively configured so as to ensure that, during the implantation procedure, only the pulling element experiences tension (the flipping element effectively remaining substantially slack) until the guide element has cleared the mouth or exit of the tunnel, for example at the cortical side of a bone. Typically, the manipulating loop will be arranged so that part of the loop remains within the bone tunnel(s) after the guide element has cleared the mouth or exit of the tunnel, at a cortical end. The manipulating loop may then be dragged through the tunnel to fully expose the loop, and subsequently used as in prior surgical practice, in conjunction with the pulling element, to orient the guide element across the mouth of the tunnel (that is, to move the guide element to the anchoring position, where it is disposed substantially perpendicularly to the pulling direction). The guide element can then rest against the bone of the tunnel mouth, thereby securing the assembly within the bone, as in prior practice.

The pulling element may comprise a leading end and a trailing end, and the pulling loop may form the trailing end. The pulling element may comprise an anchor point for the manipulating loop, by which the loop is secured to the pulling element. The pulling loop may form the leading and trailing ends (and so effectively the pulling element may take the form of a loop).

The pulling loop may comprise a portion of the pulling element which has been folded back on itself and attached to a remainder or main part of the pulling element at a location which is part way along a length thereof. Said location may define the anchor point for the manipulating loop. Said portion of the pulling element may be attached by knotting the portion to the remainder of the pulling element.

The pulling element may comprise first and second anchor points spaced along a length of the element, one of the anchor points disposed closer to the trailing end and the other disposed closer to the leading end, and the manipulating loop may be secured to the pulling element so as to be movable along the pulling element between the first and second anchor points. The pulling element may comprise an anchoring loop positioned between, and which may be defined by, the first and second anchor points, and the manipulating loop may extend through the anchoring loop so as to be secured to the pulling element and movable within the loop between the first and second anchor points.

The manipulating loop may be freely slidably movable through the anchoring loop, and along the length of the pulling element between the first and second anchor points.

The manipulating loop may be freely slidably movable between the first and second anchor points, and secured against movement (in a direction along a length of the manipulating loop) through the anchoring loop. The manipulating loop may comprise a mounting which is slidable on the anchoring loop between the first and second anchor points, the mounting restricting movement of the manipulating loop through the anchoring loop. This may provide the advantage that movement of the manipulating loop through the anchoring loop, and so translation of the manipulating loop along its length through the anchoring loop, is restricted. This may be desirable, for example, where the manipulating loop is formed so that it includes a knot, by restricting the possibility of the knot coming into contact with the guide element or an anchor point. The mounting may be a knot.

The manipulating loop may be secured to the pulling element at the anchor point, so that sliding movement of the manipulating loop relative to the anchor point is prevented. Where the anchor point is a knot, the manipulating loop may be captured (and so secured) by the knot.

The manipulating loop may have a length which is sufficiently greater than a length of the pulling loop so that, when the pulling loop and the guide element are in-line (and so with the guide element in the pulling position), the manipulating loop remains slack.

The pulling loop may have a length, the manipulating loop may have a length, and the length of the manipulating loop may be greater than a distance which is the sum of the length of the pulling loop and a spacing between the pulling aperture and the manipulating aperture. In this way, when the tensile load is applied to the pulling element to pull the guide element, trailing ligament and manipulating loop through the bone tunnels, the generation of a tensile load in the manipulating loop is avoided (and so the manipulating loop will remain substantially slack). The length of the manipulating loop may be the maximum distance between the trailing end of the pulling element (defined by the loop) and the anchor point. The spacing between the pulling and manipulating apertures may be that which is defined by a straight line extending parallel to the longitudinal axis of the guide element between an edge or surface of the pulling aperture which is closest to the leading end of the guide element, and a corresponding edge or surface of the manipulating aperture. It will be understood that the lengths of the pulling and manipulating loops should be taken when the loops are tense and so defining their maximum longitudinal extents.

The pulling loop and/or the manipulating loop may be formed by securing a length of elongate multi-stranded filamentous yarn or a monofilament to itself using a knot. Alternatively, the pulling loop and/or manipulating loop may comprise a cohesive assembly of twisted filaments, and/or may be an endless loop, manufactured according to the teachings of International Patent Publication No. WO-99/47079, the disclosure of which is incorporated herein by way of reference.

The assembly may comprise a connecting loop for connecting the ligament to the guide element, the connecting loop being connected to the connecting arrangement of the guide element. The connecting arrangement may comprise a pair of apertures disposed between the pulling and manipulating apertures, the connecting loop passing through the connecting apertures so as to trail behind the guide element when the guide element is in the pulling position. The pulling and manipulating apertures may together form the connecting arrangement, the connecting loop passing through the apertures so as to trail behind the guide element when the guide element is in the pulling position. The connecting loop may comprise a cohesive assembly of twisted filaments, and/or may be an endless loop, manufactured according the teachings of International Patent Publication No. WO-99/47079, the disclosure of which is incorporated herein by way of reference. Alternatively, the connecting loop may be formed by securing a length of elongate cord or monofilament to itself using a knot.

The connecting arrangement may be arranged to directly receive the ligament. The connecting arrangement may comprise a generally central waist portion of the guide element, which is of a smaller width (taken transverse to the longitudinal axis of the element) relative to adjacent portions of the guide element defining the leading and trailing ends. The waist portion may be adapted so that the ligament can pass around the guide element in the area of the waist portion for connecting the ligament to the guide element.

The connecting arrangement may comprise a pair of apertures disposed between the pulling and manipulating apertures. The pulling and manipulating apertures may together form the connecting arrangement. The connecting apertures, or the pulling and manipulating apertures (as appropriate), may be adapted to receive fibres of the ligament for connecting the ligament to the guide element. The ligament may be woven, and the apertures may be adapted to receive warp fibres of the ligament in a region of the ligament which is free from wefts.

The guide element may be a metallic element and so of a metal or metal alloy, although other materials such as plastics or fibre reinforced plastics composite materials may be employed. The guide element may be generally elongate. The guide element may take the general form of an Endobutton™.

Reference is made herein to a manipulating loop, and to the pulling element comprising a pulling loop. It will be understood that it is preferable to provide such loops. However, other configurations not requiring the use of such loops could be conceived, and are within the scope of the invention.

The assembly may comprise a prosthetic ligament. In the context of the invention, the term 'prosthetic' encompasses replacement of a damaged natural ligament with a ligament which can be of synthetic material or biological tissue (autogenous or allogenic).

According to a second aspect of the invention, there is provided a method of implanting a prosthetic ligament at a required position in a bone tunnel formed in a joint between two adjacent bones, and of anchoring one end of the ligament, the method comprising the steps of:
  connecting the prosthetic ligament to a connecting arrangement of a guide element which is manipulatable between:
    a pulling position in which a longitudinal axis of the guide element extends generally parallel to a pulling direction; and
    an anchoring position in which its longitudinal axis extends transversely of the pulling direction;
  the guide element defining a leading end and a trailing end, a pulling aperture being provided towards the leading end, a manipulating aperture being provided towards the trailing end, and the connecting arrangement being provided between the leading and trailing ends;
  coupling a pulling element comprising a pulling loop to the guide element, the pulling loop passing through the pulling aperture;
  coupling a manipulating loop to the guide element, the manipulating loop passing through the manipulating aperture;
  securing the manipulating loop to the pulling element;
  applying a tensile load to the pulling element to pull the guide element, trailing ligament and manipulating loop through the bone tunnels with the guide element disposed in the pulling position;
  arranging the manipulating loop such that the tensile load can be applied to the pulling element without generating a tensile load in the manipulating loop which could otherwise cause the guide element to be manipulated towards the anchoring position during passage along the bone tunnels; and
  when the guide element emerges from a mouth at the end of the tunnel, using the manipulating loop to manipulate the guide element to the anchoring position where the guide element overlies the tunnel mouth, to facilitate anchoring of the end of the ligament.

Following manipulation of the guide element to the anchoring position, the pulling loop and manipulating loop may be released from the guide element, optionally by severing the loops. Where the loops are formed using a knot, the method may comprise severing the loops proximate to the knots, suitably at a location immediately adjacent to the knots. The severed loops can then be removed by pulling on the knots, to draw the severed loops through the respective apertures of the guide elements, thereby releasing them from the guide element.

Further features of the method of the second aspect of the invention may be derived from the text set out above relating to the assembly of the first aspect of the invention.

According to a third aspect of the invention, there is provided an implantation assembly for a prosthetic ligament, for guiding the ligament to a required position in a bone tunnel formed in a joint between two adjacent bones, and for anchoring one end of the ligament, the assembly comprising:
  a guide element for the ligament, the guide element being manipulatable between a pulling position in which a longitudinal axis of the guide element extends generally parallel to a pulling direction and an anchoring position in which its longitudinal axis extends transversely of the pulling direction;
  a pulling element comprising a pulling loop for pulling the guide element through the bone tunnels; and
  a manipulating loop for manipulating the guide element to overlie a mouth at an end of one of the bone tunnels;
  in which:
  in the pulling position, the guide element defines a leading end and a trailing end, a pulling aperture being provided towards the leading end, a manipulating aperture being provided towards the trailing end, and a connecting arrangement by which the ligament can be connected to the guide element being provided between the leading and trailing ends;
  the pulling loop extends through the pulling aperture so that the pulling element can be used to pull the guide element and the trailing ligament through the bone tunnels with the guide element disposed in the pulling position;
  the manipulating loop extends through the manipulating aperture so that, when the guide element emerges from the mouth at the end of the tunnel, the manipulating loop can be used to manipulate the guide element to the anchoring position where the guide element can overlie the tunnel mouth, to facilitate anchoring of the end of the ligament;
  the manipulating loop is secured to the pulling element and arranged so that the pulling element can be used to apply a tensile load to the leading end of the guide element to pull the guide element, trailing ligament and manipulating loop through the bone tunnels without causing the manipulating loop to impart a force on the trailing end of the guide element which could otherwise cause the guide element to be manipulated towards the anchoring position during passage along the tunnels.

Further features of the assembly of the third aspect of the invention may be derived from the text set out above relating to the assembly of the first aspect of the invention.

Embodiments of the present invention will now be described, by way of example only, in which:

FIG. 1 is a schematic side view of a typical type of bone joint with which the invention may be used, and which comprises a knee joint which comprises a tibial component and a femoral component;

FIG. 2 a view of an implantation assembly for a prosthetic ligament in accordance with an embodiment of the present invention, for guiding an implant to a required position in the bone joint of FIG. 1;

FIGS. 6 and 7 (on same sheet as FIG. 2) are enlarged views of parts of the implantation assembly shown in FIG. 2;

Figure 1:
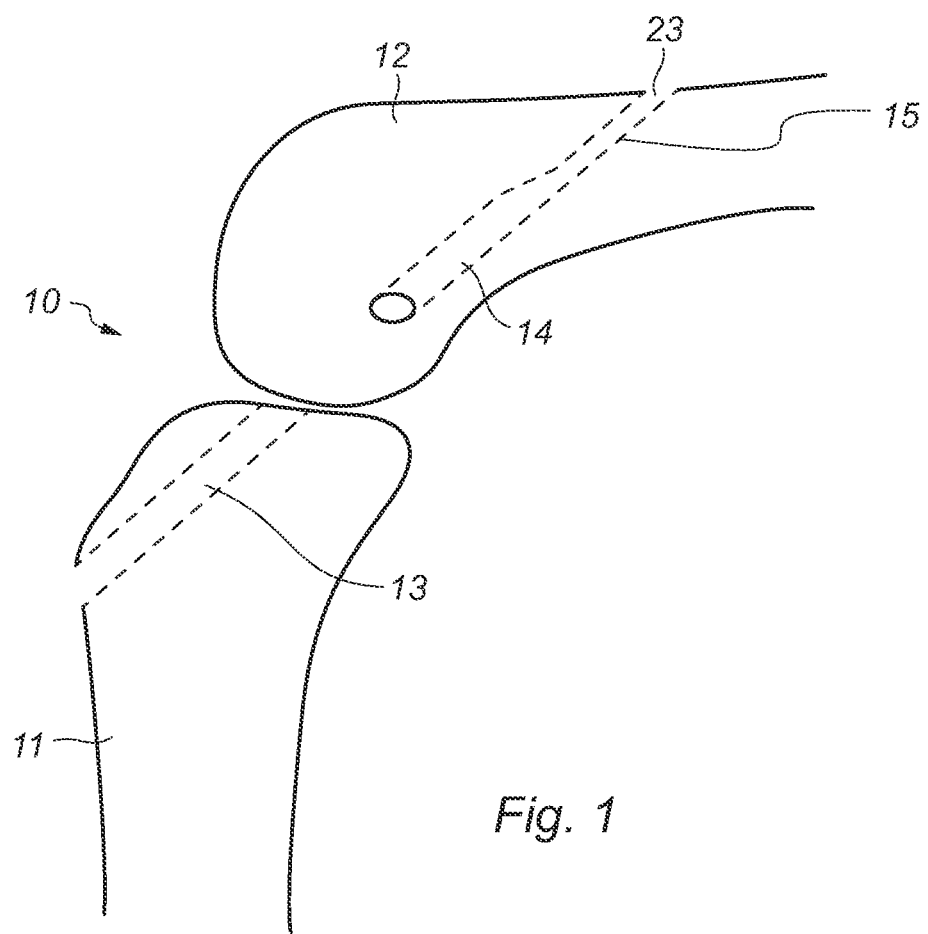
Figure 8:
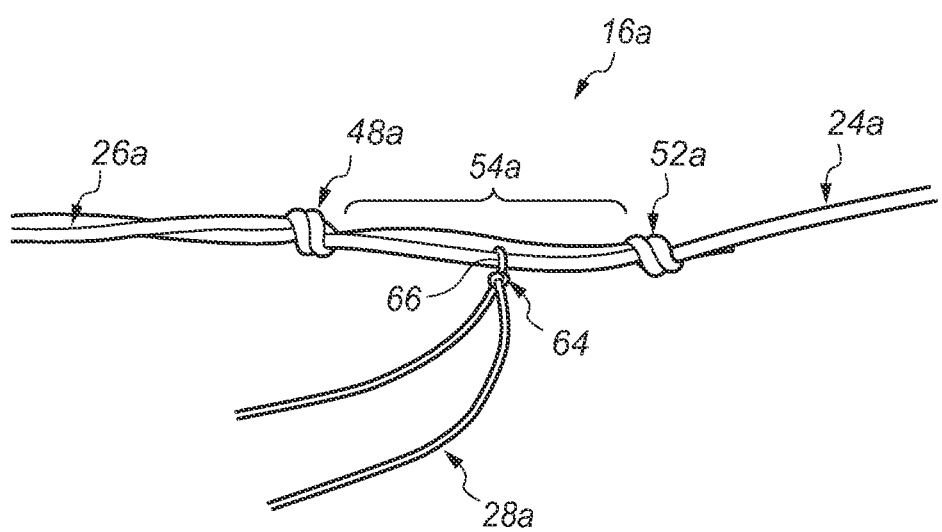
Figure 9:
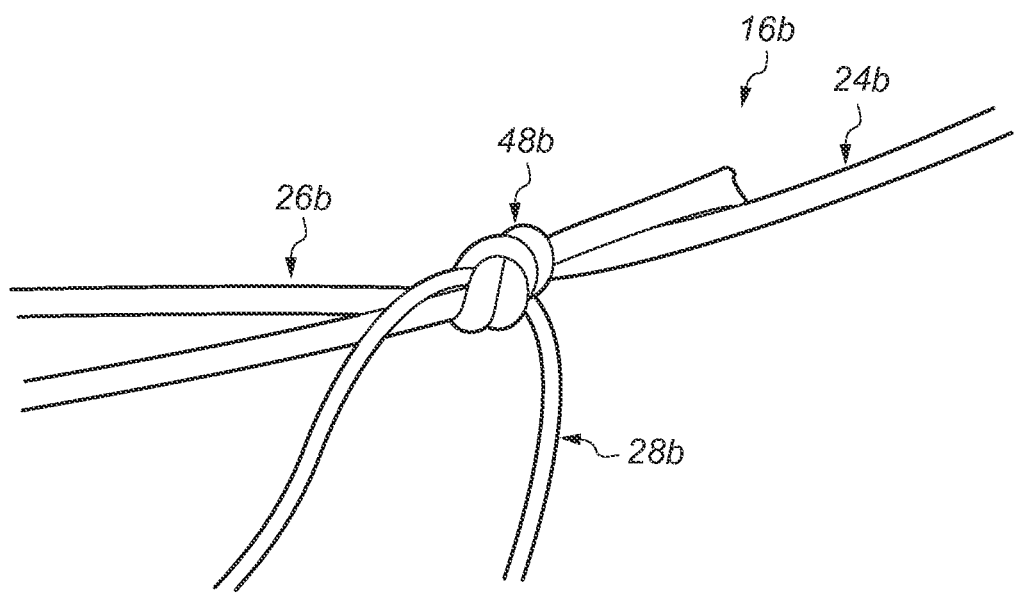

FIG. 8 a view of an implantation assembly for a prosthetic ligament in accordance with another embodiment of the present invention, for guiding an implant to a required position in the bone joint of FIG. 1; and FIG. 9 a view of an implantation assembly for a prosthetic ligament in accordance with a further embodiment of the present invention, for guiding an implant to a required position in the bone joint of FIG. 1.

Referring first to FIG. 1 of the drawings, there is shown a schematic side view of a typical type of bone joint with which the invention may be used, and which comprises a knee joint 10 which comprises a tibial component 11 and a femoral component 12. Enlarged bone tunnels 13 and 14 are drilled through the components 11 and 12, and in which a prosthetic ligament is to be implanted, but it will be noted that the bone tunnel 14 merges into a passage 15 of smaller diameter, the purpose of which will be explained in more detail below.

The described embodiments of the invention provide implantation assemblies for a prosthetic ligament, which serve to guide the ligament to a required position in a bone tunnel formed in a bone joint between two adjacent bones, and also serves to anchor a leading end of the ligament.

Accordingly, and turning now to FIG. 2, there is shown an implantation assembly for a prosthetic ligament, the assembly indicated generally by reference numeral 16, and the ligament by reference numeral 18. In the illustrated embodiment, the prosthetic ligament 18 is a woven synthetic material ligament, but may comprise autogenous or allogenic biological tissue. The implantation assembly 16 can be used to guide the ligament 18 to a required position in the bone tunnel formed in a bone joint between two adjacent bones, in this case in the bone tunnels 13 and 14 in the knee joint 10 shown in FIG. 1. The implantation assembly 16 also serves to anchor a leading end 20 of the ligament 18.

Figure 3:
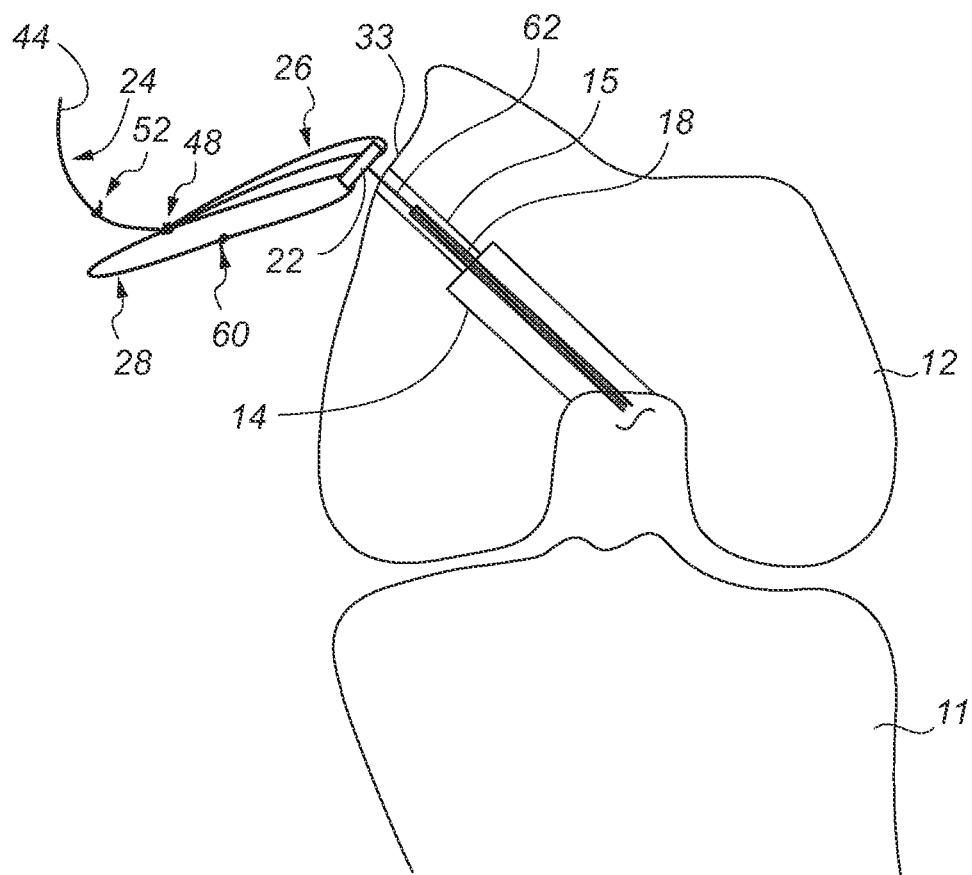
FIG. 3 is a front view of the knee joint of FIG. 1, showing the implantation assembly of FIG. 2 following location at the required position.

The implantation assembly 16 generally comprises a guide element 22 for the ligament 18, a pulling element 24 comprising a pulling loop 26 for pulling the guide element 22 through the bone tunnels 13 and 14, and a manipulating loop 28. The manipulating loop 28 is for manipulating the guide element 22 to overlie a mouth 23 at an end of the bone tunnel 14, as shown in the schematic front view of FIG. 3, showing the assembly 16 located at the required position.

Figure 4:
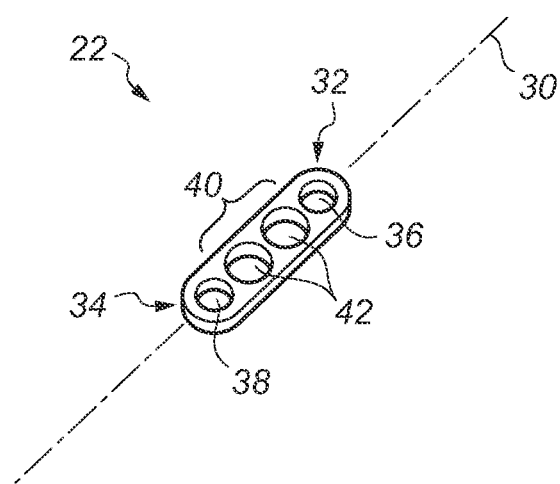
FIG. 4 is an enlarged perspective view of a guide element forming part of the implantation assembly of FIG. 2.

The guide element 22 is a generally elongate element, and is typically metallic, of a suitable metal or metal alloy material. In particular, the guide element 22 can take the form of a metal bar, and may take the form of an Endobutton™, such as that which is commercially available from Smith & Nephew in the UK. The guide element 22 is shown separately in the enlarged perspective view of FIG. 4, and is manipulatable between a pulling position, which is shown in the highly schematic view of FIG. 5, and an anchoring position, which is shown in FIG. 3. In the pulling position, a longitudinal axis 30 of the guide element 22 extends generally parallel to a pulling direction through the bone tunnels 13 and 14, whilst in the anchoring position, the longitudinal axis 30 extends transversely of the pulling direction, and is typically oriented perpendicular to the pulling direction (this depending upon features including the angle of the bone tunnel 14 relative to the general plane of the bone surface 33, and bone surface features).

When a tensile load is applied to the pulling element 24, the guide element 22 orientates itself so that its longitudinal axis 30 extends generally parallel to the axes of the tunnels 13 and 14 and in the pulling direction, so that it presents minimum lateral projection from this axis. The metal bar forming the guide element 22 typically has a length of around 12 mm, a width of around 4 mm, and a thickness of around 1.5 mm. The final passage 15 in the femoral component 12 is therefore formed so that it is slightly larger in diameter than the transverse dimension of the guide element 22, thereby allowing the pulling element 24 to pull the guide element 22 through bone tunnel 14 and narrow passage 15, and then emerging from the mouth 23. FIG. 3 shows the guide element 22 after it has been manipulated to a transversely extending position in which it overlies the mouth 23, and thereby provides anchorage for the leading end 20 of the ligament 18.

In the pulling position of the guide element 22 (in FIG. 2), it defines a leading end 32 and a trailing end 34, a pulling aperture 36 being provided towards the leading end 32, a manipulating aperture 38 being provided towards the trailing end 34, and a connecting arrangement 40 being provided between the leading and trailing ends 32 and 34. The connecting arrangement 40 serves for connecting the ligament 18 to the guide element 22 and, in the illustrated embodiment, comprises a pair of connecting apertures 42, the purpose of which will be described below. In a variation on the illustrated embodiment (not shown), the pulling and manipulating apertures 36 and 38 may define the connecting arrangement 40, in which case the apertures will typically be of larger dimension and which may be elongated in a length direction of the guide element 22.

As shown in FIG. 2, and the enlarged view of FIG. 6, the pulling loop 26 of the pulling element 24 passes through the pulling aperture 36, so that the pulling element 24 can be used to pull the guide element 22 and trailing ligament 18 through the bone tunnels 13 and 14 with the guide element disposed in the pulling position. The manipulating loop 28 passes through the manipulating aperture 38 so that, when the guide element 22 emerges from the mouth 23 at the end of the tunnel 14, the manipulating loop can be used to manipulate the guide element 22 to the anchoring position (FIG. 3), where the guide element can overlie the tunnel mouth. This facilitates subsequent anchoring of the end 20 of the ligament 18, by contact between the surface 33 of the femoral component 12 and the guide element 22.

As also shown in FIG. 2, and the enlarged view of FIG. 7, the manipulating loop 28 is secured to the pulling element 24 so that the manipulating loop can be pulled along the bone tunnels 13 and 14 by the pulling element. The manipulating element 28 is also arranged such that a tensile load can be applied to the pulling element 24 to pull the guide element 22, trailing ligament 18 and manipulating loop 28 through the bone tunnels 13 and 14 without generating a tensile load in the manipulating loop 28 which could otherwise cause the guide element to be manipulated towards the anchoring position during passage along the bone tunnels. The invention thereby addresses the potential difficulties with prior assemblies, by preventing inadvertent flipping of the guide element 22.

The implantation assembly 16, and its method of use to implant the ligament 18, will now be described in more detail.

The pulling element 24 is a multi-stranded filamentous yarn, which may be wound or braided, but could be a monofilament. The pulling element 24 is typically formed of a suitable implantable material, or of a material which is suitable for coming into contact with body tissue. The pulling element 24 comprises a leading end 44 and a trailing end 46, which is defined by the pulling loop 26. The pulling element 24 also comprises an anchor point 48, which is formed by folding the cord forming the pulling element 24 back on itself, to form the pulling loop 26, and then knotting the cord to a remainder or main part 50 of the pulling element. In the embodiment of FIG. 2, the knot which defines the anchor point 48 forms a first anchor point, and a second anchor point 52 is formed, spaced along a length of the pulling element 24 from the first anchor point. The second anchor point again takes the form of a knot. In this way, an anchoring loop 54 is formed between the first and second knots 48 and 52. The manipulating loop 28 extends through the anchoring loop 54, and is thereby secured to the pulling element 24 in such a way that the manipulating loop is moveable within the anchoring loop between the first and second knots 48 and 52.

In use, when the implantation assembly 16 is dragged through the bone tunnels 13 and 14, (in FIG. 1) the manipulating loop 28 will slide along the anchoring loop 54 until it comes into contact with the knot forming the first anchor point 48. In this way, the manipulating loop 28 will be dragged along the tunnels 13 and 14 by the pulling element 24.

The manipulating loop 28 is also typically of a multi-stranded filamentous yarn of implantable material (or material suitable for coming into contact with body tissue), but again may be a monofilament. The manipulating loop 28 is formed by threading the cord through the anchoring loop 54, manipulating aperture 38 on guide element 22 and then knotting its two ends 56 and 58 together to form a knot 60.

As can be appreciated from FIGS. 2 and 3, part of the manipulating loop 28 may remain within the bone tunnel 14, in particular the smaller diameter passage 15, following emergence of the guide element 22 from the tunnel mouth 23. A surgeon would therefore draw the remaining portion of the manipulating loop 28 up out of the passage 15, and the loop can then be tensioned to a sufficient degree to manipulate the guide element 22 to the anchoring position. A tensile force can then be exerted on the ligament 18 extending back down through the tunnel 13 in the tibial component 11, so that the guide element 22 sits on the bone surface 33, anchoring the end 20 of the ligament 18.

Following manipulation of the guide element 22 to the anchoring position, the pulling loop 26 and manipulating loop 28 are released from the guide element 22, by severing the loops. The loops 26 and 28 are severed proximate to the respective knots 48 and 60, suitably at a location immediately adjacent to the knots. The severed loops 26 and 28 can then be removed by pulling on the knots 48 and 60, to draw the severed loops through the respective apertures 36 and 38 of the guide element 22, thereby releasing the loops from the guide element.

The ligament 18 is connected to and so suspended from the guide element 22 by means of a connecting loop 62, which is typically a cohesive assembly of twisted filaments in the form of an endless loop, manufactured according to the teachings of WO-99/47079. The connecting loop 62 passes through the connecting apertures 42 in the guide element 22, and the ligament 18 is threaded through the loop 62. In this way, when the guide element 22 is drawn through the bone tunnels 13 and 14, the ligament 18 trails the guide element and so is drawn through the bone tunnels. Reference is made herein to the guide element taking up a pulling position, in which the longitudinal axis 30 of the guide element extends generally parallel to the pulling direction. One factor affecting the ability of the guide element 22 to adopt a position which is precisely parallel to the pulling direction is the relative thickness of the connecting loop 62. In practice, the thickness of the connecting loop 62 may be such that the guide element 22 lies at an angle which is slightly displaced from (and so slightly non-parallel to) the pulling direction.

Figure 5:
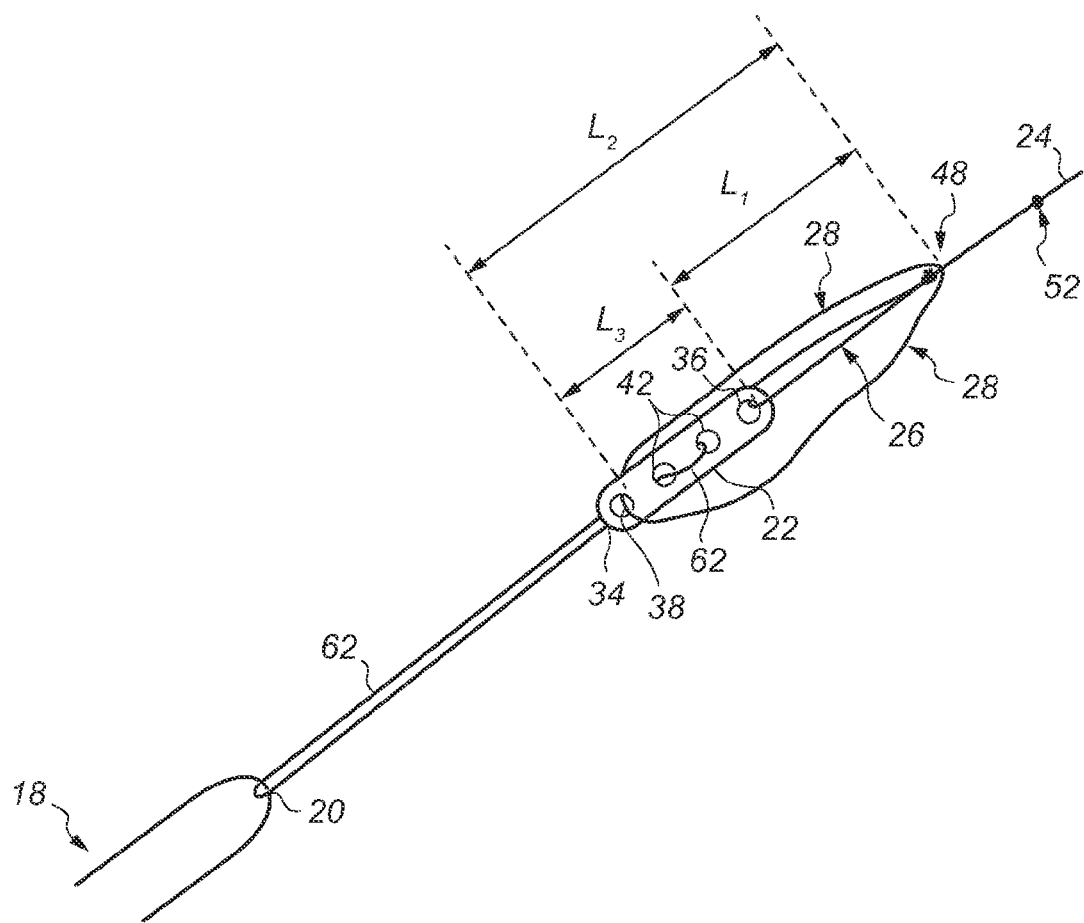
FIG. 5 is a schematic view of the implantation assembly of FIG. 2, showing the guide element of FIG. 4 in a pulling position.

The arrangement whereby a tensile load can be applied to the pulling element 24 without generating a tensile load in the manipulating loop 28 is as follows. As shown in FIG. 5, the pulling loop 26 of the pulling element 24 is of a length $L_1$ (when tense) between the trailing end 46 of the pulling element 24 and a leading side of the knot 48. The manipulating loop 28 is slack when the assembly 16 is in the position of FIG. 5, during passage along the bone tunnels 13 and 14. The manipulating loop 28 has a length which is greater than a distance $L_2$, which is the sum of the length $L_1$ of the pulling loop 26 and a spacing $L_3$ between the pulling and manipulating apertures 36 and 38 (taken in a direction along the longitudinal axis between edges of the apertures which are closest to the leading end 32). This ensures that tensioning of the pulling element 24 cannot result in a tensile load in the manipulating loop 28 which could otherwise cause the guide element 22 to be moved towards its anchoring position, with the possibility of then becoming jammed in one of the bone tunnels 13 or 14, and in particular at an entrance to the smaller diameter passage 15.

Turning now to FIG. 8, there is shown an implantation assembly in accordance with another embodiment of the present invention, the assembly indicated generally by reference numeral 16a. Like components of the assembly 16a with the assembly 16 of FIGS. 2 to 7 share the same reference numerals, with the addition of the suffix "a". Only the substantial differences between the assemblies 16a and 16 will be described herein in detail.

The assembly 16a is of like construction to the assembly 16, save that a manipulating loop 28a is freely slidably moveable between first and second anchor points in the form of knots 48a and 52a, but includes a mounting 64 which restricts movement of the manipulating loop 28a through an anchoring loop 54a. The mounting 64 takes the form of a knot formed in the manipulating loop 28a, which typically takes the form of a slip-knot. The knot 64 includes a mounting loop 66 which can slide along a branch 68 of the anchoring loop 54a between the knots 48a and 52a.

This provides the advantage that, whilst the manipulating loop 28a can slide between the knots 48a and 52a, the cord forming the manipulating loop 28a cannot pass through the anchoring loop 54a. This prevents the knot formed in the anchoring loop 28a (not shown—60 in FIG. 2) from coming into contact with the guide element 22, and in particular from becoming located at a position where it would reside between the bone surface 33 and the guide element 22. This also prevents the knot in the anchoring loop 28a from interfering with the anchoring loop 54a, which could hamper movement of the manipulating loop 28a along the pulling element 24a and so manipulation of the guide element 22 to the anchoring position.

Turning now to FIG. 9, there is shown an implantation assembly in accordance with another embodiment of the present invention, the assembly indicated generally by reference numeral 16b. Like components of the assembly 16b with the assembly 16 of FIGS. 2 to 7 share the same reference numerals, with the addition of the suffix "b". Again, only the substantial differences between the assemblies 16b and 16 will be described.

In this embodiment, a pulling element 24b includes only a single anchor point in the form of a knot 48b. A manipulating loop 28b is secured to the pulling element 24b at the anchor point 48b, and intertwined with the pulling element cord during formation of the knot, so that the loop 28b is captured by the knot 48b. In this way, sliding movement of the manipulating loop 28b relative to the knot 48b is prevented. In other words, the manipulating loop 28b cannot move along a length of the pulling element 24b. This again offers advantages in terms of preventing a knot (not shown) in the manipulating loop 28b from coming into contact with a guide element (also not shown—22 in FIG. 2), and also avoids the requirement to provide a second anchoring point, such as the anchor point 52, or to form an anchoring loop such as the loop 54, shown in FIG. 2.

Various modifications may be made to the foregoing without departing from the spirit or scope of the present invention.

The pulling loop may form the leading and trailing ends, and so effectively the pulling element may take the form of a loop.

The pulling loop and/or manipulating loop may comprise a cohesive assembly of twisted filaments, and/or may be an endless loop, manufactured according to the teachings of WO-99/47079.

The pulling and manipulating apertures may together form the connecting arrangement, the connecting loop passing through the apertures so as to trail behind the guide element when the guide element is in the pulling position.

The connecting apertures, or the pulling and manipulating apertures (as appropriate), may be adapted to receive fibres of the ligament for connecting the ligament to the guide element. The ligament may be woven, and the apertures may be adapted to receive warp fibres of the ligament in a region of the ligament which is free from wefts.

The connecting loop may be formed by securing a length of elongate cord or monofilament to itself using a knot.

The connecting arrangement may be arranged to directly receive the ligament. The connecting arrangement may comprise a generally central waist portion of the guide element, which is of a smaller width (taken transverse to the longitudinal axis of the element) relative to adjacent portions of the guide element defining the leading and trailing ends. The waist portion may be adapted so that the ligament can pass around the guide element in the area of the waist portion for connecting the ligament to the guide element.

Reference is made herein to a manipulating loop, and to the pulling element comprising a pulling loop. Other configurations not requiring the use of such loops could be conceived, and are within the scope of the invention.

The invention claimed is:

1. An implantation assembly for a prosthetic ligament, for guiding the ligament to a required position in bone tunnels formed in a joint between two adjacent bones, and for anchoring one end of the ligament, the assembly comprising:
    a guide element for the ligament, the guide element being manipulatable between a pulling position in which a longitudinal axis of the guide element extends parallel or generally parallel to a pulling direction and an anchoring position in which its longitudinal axis extends transversely of the pulling direction;
    a pulling element comprising a pulling loop for pulling the guide element through the bone tunnels; and
    a manipulating loop for manipulating the guide element to overlie a mouth at an end of one of the bone tunnels;
    in which:
    in the pulling position, the guide element defines a leading end and a trailing end, a pulling aperture being provided towards the leading end, a manipulating aperture being provided towards the trailing end, and a connecting arrangement by which the ligament can be connected to the guide element being provided between the leading and trailing ends;
    the pulling loop passes through the pulling aperture so that the pulling element can be used to pull the guide element and the trailing ligament through the bone tunnels with the guide element disposed in the pulling position;
    the manipulating loop passes through the manipulating aperture so that, when the guide element emerges from the mouth at the end of one of the bone tunnels, the manipulating loop can be used to manipulate the guide element to the anchoring position where the guide element can overlie the mouth at the end of one of the bone tunnels, to facilitate anchoring of the end of the ligament;
    the manipulating loop is secured to the pulling element so that the manipulating loop can be pulled along the bone tunnels by the pulling element; and
    the manipulating loop is arranged such that a tensile load can be applied to the pulling element to pull the guide element, the trailing ligament and the manipulating loop through the bone tunnels without generating a tensile load in the manipulating loop which could otherwise cause the guide element to be manipulated towards the anchoring position during passage along the bone tunnels.

2. An assembly as claimed in claim 1, in which the pulling element comprises a leading end and a trailing end, the pulling loop forming the trailing end of the pulling element, and in which the pulling element comprises an anchor point for the manipulating loop, by which the manipulating loop is secured to the pulling element.

3. An assembly as claimed in claim 2, in which the pulling loop comprises a portion of the pulling element which has been folded back on itself and attached to a main part of the pulling element at a location which is part way along a length of the pulling element, said location defining the anchor point for the manipulating loop.

4. An assembly as claimed in claim 2, in which the pulling element comprises first and second anchor points spaced along a length of the pulling element, one of the anchor points disposed closer to the trailing end of the pulling element and the other disposed closer to the leading end of the pulling element, and in which the manipulating loop is secured to the pulling element so as to be movable along the pulling element between the first and second anchor points.

5. An assembly as claimed in claim 4, in which the pulling element comprises an anchoring loop positioned between and defined by the first and second anchor points, and in which the manipulating loop extends through the anchoring loop so as to be secured to the pulling element and is movable within the anchoring loop between the first and second anchor points.

6. An assembly as claimed in claim 5, in which the manipulating loop is freely slidably movable through the anchoring loop, and along the length of the pulling element between the first and second anchor points.

7. An assembly as claimed in claim 5, in which the manipulating loop is freely slidably movable between the first and second anchor points, and secured against movement through the anchoring loop.

8. An assembly as claimed in claim 7, in which the manipulating loop comprises a mounting which is slidable on the anchoring loop between the first and second anchor points, the mounting restricting movement of the manipulating loop through the anchoring loop.

9. An assembly as claimed in claim 8, in which the mounting is a slip-knot.

10. An assembly as claimed in claim 2, in which the manipulating loop is secured to the pulling element at the anchor point, so that sliding movement of the manipulating loop relative to the anchor point is prevented.

11. An assembly as claimed in claim 10, in which the anchor point is a knot, and in which the manipulating loop is captured by the knot.

12. An assembly as claimed in claim 1, in which the pulling loop forms leading and trailing ends of the pulling element.

13. An assembly as claimed in claim 1, in which the manipulating loop has a length which is greater than a length of the pulling loop so that, when the pulling loop and the guide element are in-line, the manipulating loop remains slack.

14. An assembly as claimed in claim 1, in which the pulling loop has a length, the manipulating loop has a length, and in which the length of the manipulating loop is greater than a distance which is a sum of the length of the pulling loop and a spacing between the pulling aperture and the manipulating aperture.

15. An assembly as claimed in claim 14, in which the length of the manipulating loop is a maximum distance between the trailing end of the pulling element and the anchor point; and the spacing between the pulling and manipulating apertures is that which is defined by a straight line extending parallel to the longitudinal axis of the guide element between an edge of the pulling aperture which is closest to the leading end of the guide element, and a corresponding edge or surface of the manipulating aperture.

16. An assembly as claimed in claim 1, comprising a connecting loop for connecting the ligament to the guide element, the connecting loop being connected to the connecting arrangement of the guide element.

17. A method of implanting a prosthetic ligament at a required position in bone tunnels formed in a joint between two adjacent bones, and of anchoring one end of the ligament, the method comprising the steps of:
connecting the prosthetic ligament to a connecting arrangement of a guide element which is manipulatable between:
a pulling position in which a longitudinal axis of the guide element extends parallel or generally parallel to a pulling direction; and
an anchoring position in which its longitudinal axis extends transversely of the pulling direction;
the guide element defining a leading end and a trailing end, a pulling aperture being provided towards the leading end, a manipulating aperture being provided towards the trailing end, and the connecting arrangement being provided between the leading and trailing ends;
coupling a pulling element comprising a pulling loop to the guide element, the pulling loop passing through the pulling aperture;
coupling a manipulating loop to the guide element, the manipulating loop passing through the manipulating aperture;
securing the manipulating loop to the pulling element;
applying a tensile load to the pulling element to pull the guide element, trailing ligament and manipulating loop through the bone tunnels with the guide element disposed in the pulling position;
arranging the manipulating loop such that the tensile load can be applied to the pulling element without generating a tensile load in the manipulating loop which could otherwise cause the guide element to be manipulated towards the anchoring position during passage along the bone tunnels; and
when the guide element emerges from a mouth at an end of one of the bone tunnels, using the manipulating loop to manipulate the guide element to the anchoring position where the guide element overlies the mouth at the end of one of the bone tunnels, to facilitate anchoring of the end of the ligament.

18. A method as claimed in claim 17, in which the pulling loop and manipulating loop are each formed using a knot, and in which, following manipulation of the guide element to the anchoring position, the pulling loop and manipulating loop are released from the guide element by severing the pulling and manipulating loops and then pulling on the knots to draw the severed pulling and manipulating loops through the respective apertures of the guide elements.

19. A method as claimed in claim 18, comprising severing the pulling and manipulating loops at a location immediately adjacent to the knots.

20. An implantation assembly for a prosthetic ligament, for guiding the ligament to a required position in bone tunnels formed in a joint between two adjacent bones, and for anchoring one end of the ligament, the assembly comprising:
a guide element for the ligament, the guide element being manipulatable between a pulling position in which a longitudinal axis of the guide element extends parallel or generally parallel to a pulling direction and an anchoring position in which its longitudinal axis extends transversely of the pulling direction;
a pulling element comprising a pulling loop for pulling the guide element through the bone tunnels; and
a manipulating loop for manipulating the guide element to overlie a mouth at an end of one of the bone tunnels;
in which:
in the pulling position, the guide element defines a leading end and a trailing end, a pulling aperture being provided towards the leading end, a manipulating aperture being provided towards the trailing end, and a connecting arrangement by which the ligament can be connected to the guide element being provided between the leading and trailing ends;
the pulling loop extends through the pulling aperture so that the pulling element can be used to pull the guide element and the trailing ligament through the bone tunnels with the guide element disposed in the pulling position;
the manipulating loop extends through the manipulating aperture so that, when the guide element emerges from the mouth at the end of one of the bone tunnels, the manipulating loop can be used to manipulate the guide element to the anchoring position where the guide element can overlie the mouth at the end of one of the bone tunnels, to facilitate anchoring of the end of the ligament;

the manipulating loop is secured to the pulling element and arranged so that the pulling element can be used to apply a tensile load to the leading end of the guide element to pull the guide element, trailing ligament and manipulating loop through the bone tunnels without causing the manipulating loop to impart a force on the trailing end of the guide element which could otherwise cause the guide element to be manipulated towards the anchoring position during passage along the bone tunnels.

\* \* \* \* \*